(12) United States Patent
Chang

(10) Patent No.: US 9,092,557 B2
(45) Date of Patent: Jul. 28, 2015

(54) ANALYTE-TESTING DEVICE

(71) Applicant: Bayer HealthCare LLC, Whippany, NJ (US)

(72) Inventor: Kevin Chang, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 14/579,571

(22) Filed: Dec. 22, 2014

(65) Prior Publication Data

US 2015/0109141 A1     Apr. 23, 2015

Related U.S. Application Data

(60) Division of application No. 14/174,716, filed on Feb. 6, 2014, which is a continuation of application No. 13/657,433, filed on Oct. 22, 2012, now Pat. No. 8,679,847, which is a continuation of application No. 12/523,498, filed as application No. PCT/US2008/000761 on Jan. 22, 2008, now Pat. No. 8,309,357.

(60) Provisional application No. 60/881,983, filed on Jan. 23, 2007.

(51) Int. Cl.
*G01N 15/06*     (2006.01)
*G01N 33/00*     (2006.01)
*G01N 33/48*     (2006.01)
*G06F 19/00*     (2011.01)

(52) U.S. Cl.
CPC .................................. *G06F 19/3418* (2013.01)

(58) Field of Classification Search
USPC ........ 436/43, 44, 63, 65, 66, 71, 174; 422/50, 422/68.1
See application file for complete search history.

(56) References Cited

U.S. PATENT DOCUMENTS

| 5,182,707 | A | 1/1993 | Cooper et al. |
| 5,190,863 | A | 3/1993 | Magers |
| 5,264,348 | A | 11/1993 | Schick et al. |

(Continued)

FOREIGN PATENT DOCUMENTS

| EP | 0637808 | 2/1995 |
| WO | 2005/040793 | 5/2005 |
| WO | 2006/066038 | 6/2006 |

OTHER PUBLICATIONS

International Search Report corresponding to International Patent Application No. PCT/US2008/000761, European Patent Office, dated Apr. 12, 2008, 3 pages.

(Continued)

*Primary Examiner* — Brian J Sines
(74) *Attorney, Agent, or Firm* — Nixon Peabody LLP

(57) ABSTRACT

A device adapted to determine an analyte concentration of a fluid sample using a test sensor. The device comprises a display adapted to display information to a user. The device further comprises at least one user-interface mechanism adapted to allow the user to interact with the device. The device further comprises a body portion including at least one opening formed therein, the at least one opening being of sufficient size to receive the test sensor. The device further comprises a memory adapted to store a plurality of stored analyte concentrations. The device further comprises a processing feature adapted to inhibit the stored analyte concentrations from being displayed on the display.

10 Claims, 2 Drawing Sheets

(56) References Cited

U.S. PATENT DOCUMENTS

| | | | |
|---|---|---|---|
| 5,307,263 | A | 4/1994 | Brown |
| 5,326,697 | A | 7/1994 | Magers |
| 5,510,245 | A | 4/1996 | Magers |
| 5,593,390 | A | 1/1997 | Castellano et al. |
| 5,665,215 | A | 9/1997 | Bussmann et al. |
| 5,728,074 | A | 3/1998 | Castellano et al. |
| 5,747,666 | A | 5/1998 | Willis |
| 5,925,021 | A | 7/1999 | Castellano et al. |
| 6,562,625 | B2 | 5/2003 | Modzelewski et al. |
| 6,612,983 | B1 | 9/2003 | Marchal |
| 6,673,617 | B2 | 1/2004 | Patel |
| 6,878,517 | B1 | 4/2005 | Benson |
| 7,344,626 | B2 | 3/2008 | Harding et al. |
| 2003/0191415 | A1 | 10/2003 | Moerman et al. |
| 2004/0030578 | A1 | 2/2004 | Cross et al. |
| 2005/0038332 | A1 | 2/2005 | Saidara et al. |
| 2005/0143675 | A1 | 6/2005 | Neel et al. |
| 2005/0258050 | A1 | 11/2005 | Harding |
| 2005/0283380 | A1 | 12/2005 | Garduno |
| 2006/0073097 | A1 | 4/2006 | Ma et al. |
| 2006/0094986 | A1 | 5/2006 | Neel et al. |
| 2006/0189895 | A1 | 8/2006 | Neel et al. |
| 2007/0231846 | A1 | 10/2007 | Cosentino et al. |
| 2008/0083618 | A1 | 4/2008 | Neel et al. |
| 2009/0012374 | A1 | 1/2009 | Schmelzeisen-Redeker et al. |
| 2009/0197283 | A1 | 8/2009 | Gold et al. |

OTHER PUBLICATIONS

Written Opinion corresponding to International Patent Application No. PCT/US2008/000761, European Patent Office, dated Apr. 12, 2008, 7 pages.

ANALYTE-TESTING DEVICE

CROSS-REFERENCE TO RELATED APPLICATIONS

This application is a divisional of U.S. patent application Ser. No. 14/174,716, filed Feb. 6, 2014, which is a continuation of U.S. patent application Ser. No. 13/657,433, filed Oct. 22, 2012, which is a continuation of U.S. patent application Ser. No. 12/523,498, filed Jul. 16, 2009, which is a U.S. national phase of International Application No. PCT/US2008/000761, filed Jan. 22, 2008, which claims the benefit of priority of U.S. Provisional Application No. 60/881,983, filed Jan. 23, 2007, all of which are incorporated by reference in their entireties.

FIELD OF THE INVENTION

The present invention relates generally to an analyte-testing device and, more particularly, to a meter adapted to limit the analyte concentrations that are viewable during testing and a method of performing the same.

BACKGROUND OF THE INVENTION

The quantitative determination of analytes in body fluids is of great importance in the diagnoses and maintenance of certain physiological abnormalities. For example, lactate, cholesterol, and bilirubin should be monitored in certain individuals. In particular, determining glucose in body fluids is important to diabetic individuals who must frequently check the glucose level in their body fluids to regulate the glucose intake in their diets. The results of such tests may be used to determine what, if any, insulin and/or other medication needs to be administered. In one type of testing system, test sensors are used to test a fluid such as a sample of blood.

One method of monitoring an individual's blood glucose level is with a portable, hand-held blood glucose testing device (e.g., a meter). To determine the blood glucose level with the meter, a lancet device may be used with a needle lancet that pierces the skin tissue and allows a whole blood sample to form on the skin's surface. Once the requisite amount of blood forms on the skin's surface, the blood sample is transferred to a test sensor. The test sensor is generally placed in an opening in the body of the meter.

Existing meters typically include a memory for storing previous analyte concentrations taken at earlier times. The stored test results are generally stored within the memory until they are transferred to another device having a larger memory (e.g., a computer) or deleted. Furthermore, meters generally include a scroll button or other type of user-interface mechanism that allows a user to review stored test results.

A problem occurs when the stored test results are accidentally accessed by the user (e.g., by accidentally pressing the scroll button). For example, a user testing his or her glucose concentration may accidentally and/or unknowingly press the scroll button during testing, thereby causing the user to mistake a glucose concentration associated with a previous testing procedure for the user's current glucose concentration. Such mistaken test results may result in unsafe glucose levels (e.g., hyperglycemic or hypoglycemic conditions) being undetected, which may be dangerous for a user and may have serious health-related consequences.

It would be desirable to provide an analyte-testing device that assists in addressing the above disadvantages.

SUMMARY OF THE INVENTION

According to one embodiment, a device adapted to determine an analyte concentration of a fluid sample using a test sensor is disclosed. The device comprises a display adapted to display information to a user. The device further comprises at least one user-interface mechanism adapted to allow the user to interact with the device. The device further comprises a body portion including at least one opening formed therein. The at least one opening is of sufficient size to receive the test sensor. The device further comprises a memory adapted to store a plurality of stored analyte concentrations. The device further comprises a processing feature adapted to inhibit the stored analyte concentrations from being displayed on the display.

According to another embodiment, a device adapted to determine an analyte concentration of a fluid sample using a test sensor is disclosed. The device comprises a display adapted to display information to a user. The device further comprises at least one user-interface mechanism for allowing the user to interact with the device. The device further comprises a body portion including at least one opening formed therein. The at least one opening is adapted to receive a test sensor. The device further comprises a memory adapted to store a plurality of stored analyte concentrations. When the at least one opening includes a test sensor, the display is limited to displaying only information associated with a current analyte concentration.

According to one process, a method of using a device adapted to determine an analyte concentration of a fluid sample using a test sensor is disclosed. The method comprises the act of providing a device comprising a display, at least one user-interface mechanism, a body portion including at least one opening formed therein, and a memory adapted to store a plurality of stored analyte concentrations. The method further comprises the act of interacting with the at least one user-interface mechanism. The at least one user-interface mechanism is adapted to assist in displaying at least one of the plurality of stored analyte concentrations on the display. The method further comprises the act of determining whether a predetermined condition exists. The method further comprises the act of, if the predetermined condition exists, inhibiting the plurality of stored analyte concentrations from being displayed on the display.

According to another process, a method of using a device adapted to determine an analyte concentration of a fluid sample using a test sensor is disclosed. The method comprises the act of providing a device comprising a display, at least one user-interface mechanism, a body portion including at least one opening formed therein, and a memory adapted to store a plurality of stored analyte concentrations. The method further comprises the act of interacting with the at least one user-interface mechanism. The at least one user-interface mechanism is adapted to assist in displaying at least one of the plurality of stored analyte concentrations on the display. The method further comprises the act of determining whether a test sensor is positioned in the at least one opening. The method further comprises the act of, if a test sensor is positioned in the at least one opening, inhibiting the plurality of stored analyte concentrations from being displayed on the display.

The above summary of the present invention is not intended to represent each embodiment or every aspect of the present invention. Additional features and benefits of the present invention are apparent from the detailed description and figures set forth below.

DESCRIPTION OF ILLUSTRATED EMBODIMENTS

The embodiments of the present invention are directed to an analyte-testing device, or meter, having a display-inhibiting feature. More specifically, the meters of the embodiments described herein inhibit or prevent a user from accidentally and/or unknowingly viewing stored analyte concentrations from previous analyte-testing procedures.

The meters described herein may be used to assist in determining an analyte concentration in a fluid sample. Some examples of the types of analytes that may be collected and analyzed include glucose, lipid profiles (e.g., cholesterol, triglycerides, LDL, and HDL), microalbumin, hemoglobin, $A_{IC}$, fructose, lactate, or bilirubin. The present invention is not limited, however, to these specific analytes, and it is contemplated that other analyte concentrations may be determined. The analytes may be in, for example, a whole blood sample, a blood serum sample, a blood plasma sample, or other body fluids like interstitial fluid (ISF) and/or urine. One non-limiting example of a use for the test-sensor cartridge and meter is to determine the glucose concentration in a user's blood, plasma, or ISF.

Figure 1:
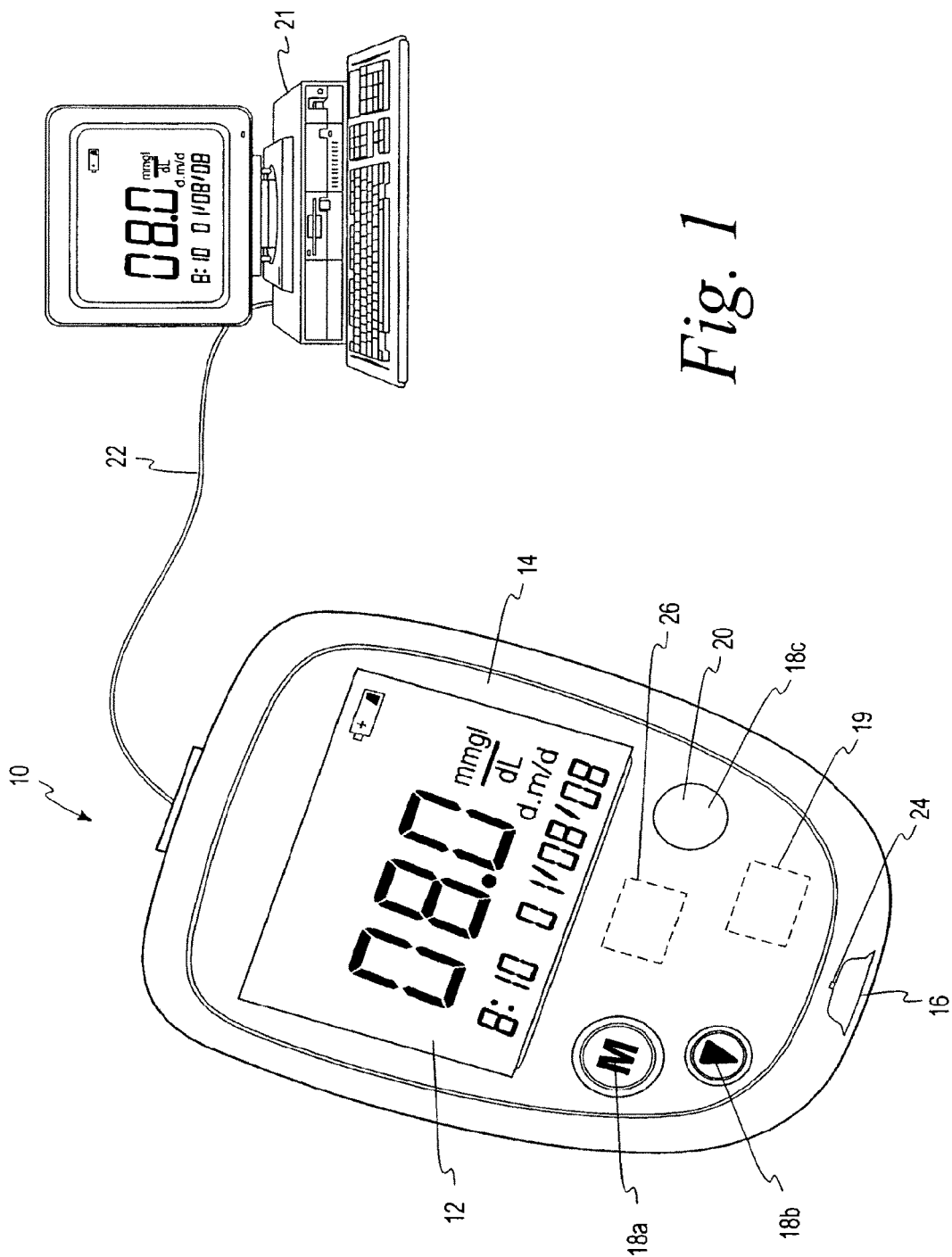
FIG. 1 is a front view of a meter according to one embodiment.

FIG. 1 illustrates a meter 10 according to one embodiment. The meter 10 includes a display 12, a body portion 14, at least one test-sensor opening, at least one user-interface mechanism 18 for allowing a user to interact with the meter 10, and a processor 26 adapted to process information. The at least one test-sensor opening includes an opening 16 adapted to receive and/or hold a test sensor. The at least one opening may also be adapted to dispense a test sensor. In the illustrated embodiment, the user-interface mechanism 18 includes a plurality of buttons 18a-c. It is contemplated that the user-interface may include other mechanisms suitable for communicating with the meter 10 including, but not limited to, a scroll wheel, touch screens, or combinations thereof Although the embodiments described herein are generally described as having one or more buttons 18a-c as the user-interface mechanism, any suitable type of user-interface mechanism or combinations thereof may be used instead of the buttons 18a-c described herein. One example of a display 12 that may be used in the meter 10 is a liquid-crystal display. The display 12 typically shows information regarding a testing procedure and/or information in response to signals input by the user-interface mechanism (e.g., buttons 18a-c). The result of the testing may also be announced audibly, by, for example, using a speaker. The meter 10 may then store the information in a memory 19.

After the testing has been completed, the test sensor may be removed from the opening 16 using one of several methods. In one embodiment, the meter 10 may include an eject mechanism 20 that ejects the used test sensor from the meter 10. In such an embodiment, the test sensor is released forcefully. In a further embodiment, the test sensor may be removed manually from the meter 10.

The memory 19 generally stores information associated with previous analyte-testing procedures. For example, the memory 19 may include previous analyte concentrations, the date and time at which the previous tests were performed, other information associated with the previous tests, combinations thereof, or the like. A user may access stored test results from the memory 19 by interacting with the user interface mechanism 18a-c. For example, the user may press a scroll button 18b to scroll through stored test results stored in the memory 19 of the meter 10. The user may link the meter 10 to another device (e.g., a computer 21) having a larger memory to copy or transfer the data to the other device. The data may be transferred using a cable 22, wirelessly, or using any other suitable means. In one embodiment, for example, the meter 10 is used with a continuous analyte monitoring assembly, which may be connected to a remote-monitoring system over a communications link.

The meters of the embodiments described herein include a display-inhibiting feature adapted to inhibit or prevent stored analyte concentrations from previous analyte-testing procedures from being displayed on the display. The display-inhibiting feature thus inhibits or prevents a user from accidentally and/or unknowingly causing stored test results to be displayed on the display. The display-inhibiting feature may, for example, be a processing feature. The display-inhibiting feature may be accomplished using software within the meter 10, hardware, or a combination thereof. For example, the feature may be associated with the processor 26.

According to one embodiment, the display-inhibiting feature is selectively activated during specific instances. For example, in one embodiment, the display-inhibiting feature is activated when a test sensor is positioned within the opening 16. Thus, when a test sensor is positioned within the opening 16, the display 12 is limited to displaying only information associated with the current analyte-testing procedure (e.g., the present analyte concentration, the present date and/or time, combinations thereof, or the like). The meter 10 may include a detector 24, a switch, or the like positioned proximate to the opening 16 that detects when a test sensor is positioned within the opening 16. It is contemplated that the display-inhibiting feature may be deactivated (e.g., information regarding stored analyte concentrations may be viewed) upon removal of the test sensor from the opening 16. Activating the display-inhibiting feature during testing procedures may be beneficial to inhibit or prevent the user from accidentally interacting with the user-interface mechanism (e.g., pressing the scroll button 18b), causing information associated with a previous testing procedure to appear on the screen, and mistaking a stored analyte concentration for the user's current analyte concentration.

Figure 2:
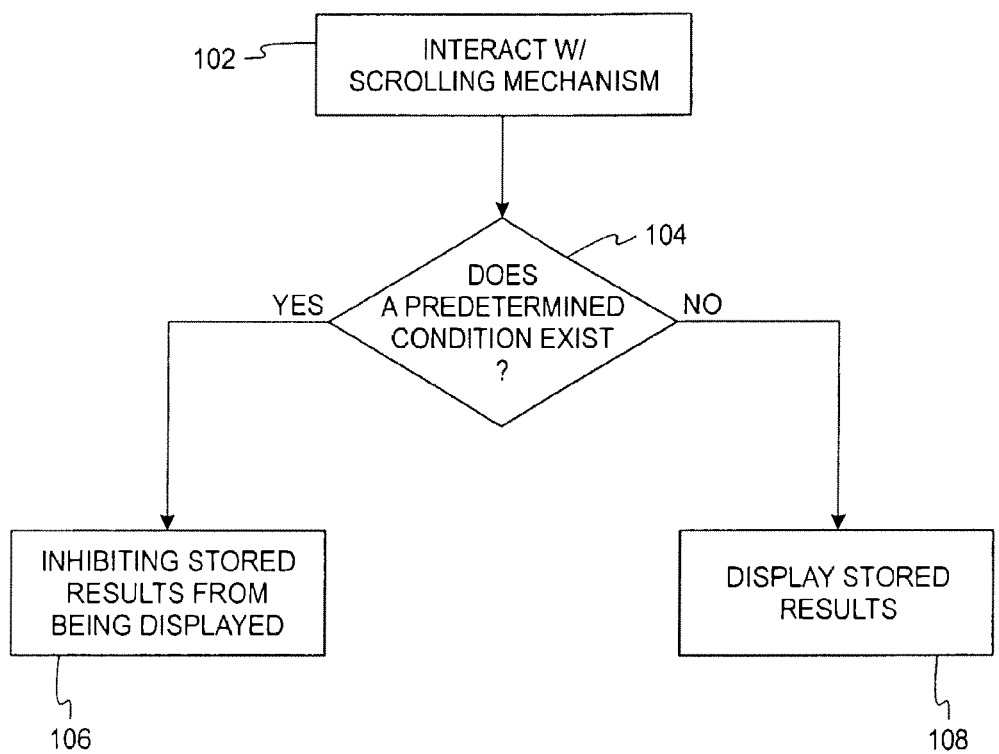
FIG. 2 is a flow diagram detailing one method of the present invention.

Turning now to FIG. 2, a flow diagram is shown according to one method of the present invention. At act 102, a user interacts with a user-interface mechanism (e.g., a scroll button 18b) positioned on the meter 10 to view stored analyte concentrations and information associated therewith. At act 104, the meter 10 determines whether a predetermined condition exists. One non-limiting example of a predetermined condition includes a test sensor being positioned within the opening 16. If at act 104, the meter 10 determines that the predetermined condition(s) exists (e.g., a test sensor is positioned within the opening 16), the stored analyte concentrations are inhibited from being displayed on the display 12 at act 106. In one embodiment, the user may receive an audible message or a message on the display 12 indicating that the scroll button 18b was pressed, that stored test results may not be viewed during a testing procedure, a combination thereof, or the like. Upon removing the sensor from the opening 16, the stored analyte concentrations may be displayed on the display 12. If, on the other hand, the meter 10 determines at act 104 that the predetermined condition(s) does not exist (e.g., a test sensor is not positioned within the opening 16), the meter 10 may display stored analyte concentrations at act 108.

According to another embodiment, the display-inhibiting feature is continuously activated such that one or more predetermined, affirmative acts must be performed each time a user desires to view stored analyte concentrations to override the display-inhibiting feature. In one non-limiting example, pressing the scroll button 18b may cause the meter 10 to prompt the user to press another button(s), to repress the scroll button 18b, to press and hold a button 18a-c, to press two or more buttons 18a-c simultaneously, or to perform some other affirmative act(s) to confirm that the user desires to view stored test results and that the scroll button 18b was not pressed accidentally. The meter 10 may prompt the user to perform such an affirmative act(s) by displaying instructions on the display 12, by audibly instructing the user, a combination thereof, or the like. The ability to override the display-inhibiting feature may be applied to meters in which the display-inhibiting feature is continuously activated or to meters in which the display-inhibiting feature is selectively activated (e.g., when a test sensor is positioned within the opening 16, as described above). It is contemplated that types of analyte-testing devices other than the meter 10 shown in FIG. 1 may be used in conjunction with any of the embodiments described herein.

Alternative Embodiment A

A device adapted to determine an analyte concentration of a fluid sample using a test sensor, the device comprising:
 a display adapted to display information to a user;
 at least one user-interface mechanism adapted to allow the user to interact with the device;
 a body portion including at least one opening formed therein, the at least one opening being of sufficient size to receive the test sensor;
 a memory adapted to store a plurality of stored analyte concentrations; and
 a processing feature adapted to inhibit the stored analyte concentrations from being displayed on the display.

Alternative Embodiment B

The device of Alternative Embodiment A, wherein the processing feature is continuously activated.

Alternative Embodiment C

The device of Alternative Embodiment A, wherein the processing feature is selectively activated.

Alternative Embodiment D

The device of Alternative Embodiment C, wherein the processing feature is activated when the at least one opening includes a test sensor.

Alternative Embodiment E

The device of Alternative Embodiment D, wherein the processing feature includes a detector proximate to the at least one opening, the detector being adapted to detect whether the at least one opening includes a test sensor.

Alternative Embodiment F

The device of Alternative Embodiment D, wherein the processing feature is adapted to deactivate the at least one user-interface mechanism.

Alternative Embodiment G

The device of Alternative Embodiment A, wherein when the processing feature is activated, the display is limited to displaying information associated with a current analyte concentration.

Alternative Embodiment H

The device of Alternative Embodiment A, wherein the processing feature may be overridden by interacting with the at least one user-interface mechanism in a predetermined manner.

Alternative Embodiment I

A device adapted to determine an analyte concentration of a fluid sample using a test sensor, the device comprising:
 a display adapted to display information to a user;
 at least one user-interface mechanism for allowing the user to interact with the device;
 a body portion including at least one opening formed therein, the at least one opening being adapted to receive a test sensor; and
 a memory adapted to store a plurality of stored analyte concentrations,
 wherein when the at least one opening includes a test sensor, the display is limited to displaying only information associated with a current analyte concentration.

Alternative Embodiment J

The device of Alternative Embodiment I, wherein upon removal of the test sensor from the at least one opening, information associated with stored analyte concentrations may be viewed.

Alternative Embodiment K

The device of Alternative Embodiment I, further including a hardware component adapted to limit the information displayed on the display.

Alternative Embodiment L

The device of Alternative Embodiment K, further comprising a detector proximate to the at least one opening, the detector being adapted to detect whether the at least one opening includes a test sensor.

Alternative Embodiment M

The device of Alternative Embodiment I, further including a software component adapted to limit the information displayed on the display.

Alternative Process N

A method of using a device adapted to determine an analyte concentration of a fluid sample using a test sensor, the method comprising the acts of:
 providing a device comprising a display, at least one user-interface mechanism, a body portion including at least one opening formed therein, and a memory adapted to store a plurality of stored analyte concentrations;
 interacting with the at least one user-interface mechanism, the at least one user-interface mechanism being adapted to assist in displaying at least one of the plurality of stored analyte concentrations on the display;
 determining whether a predetermined condition exists; and
 if the predetermined condition exists, inhibiting the plurality of stored analyte concentrations from being displayed on the display.

Alternative Process O

The method of Alternative Process N, further comprising the act of, if the predetermined condition does not exist, displaying the at least one of the plurality of stored analyte concentrations on the display.

Alternative Process P

The method of Alternative Process N, wherein the predetermined condition includes a test sensor being positioned in the at least one opening.

Alternative Process O

The method of Alternative Process N, wherein the device further includes a software component adapted to inhibit the plurality of stored analyte concentrations from being displayed on the display.

Alternative Process R

The method of Alternative Process N, wherein act of the inhibiting the plurality of stored analyte concentrations from being displayed on the display includes deactivating the user-interface mechanism.

Alternative Process S

The method of Alternative Process N, further comprising performing a predetermined act, the predetermined act assisting in displaying at least one of the plurality of stored analyte concentrations on the display.

Alternative Process T

A method of using a device adapted to determine an analyte concentration of a fluid sample using a test sensor, the method comprising the acts of:
providing a device comprising a display, at least one user-interface mechanism, a body portion including at least one opening formed therein, and a memory adapted to store a plurality of stored analyte concentrations;
interacting with the at least one user-interface mechanism, the at least one user-interface mechanism being adapted to assist in displaying at least one of the plurality of stored analyte concentrations on the display;
determining whether a test sensor is positioned in the at least one opening; and
if a test sensor is positioned in the at least one opening, inhibiting the plurality of stored analyte concentrations from being displayed on the display.

Alternative Process U

The method of Alternative Process T, further comprising the act of, if a test sensor is not positioned in the at least one opening, displaying at least one of the plurality of stored analyte concentrations on the display.

Alternative Process V

The method of Alternative Process T, further comprising the act of, upon removing the test sensor from the at least one opening, allowing the plurality of stored analyte concentrations to be displayed on the display.

Alternative Process W

The method of Alternative Process T, wherein the device further includes a software component adapted to inhibit the plurality of stored analyte concentrations from being displayed on the display.

Alternative Process X

The method of Alternative Process T, wherein the device further includes a detector positioned proximate to the at least one opening.

Alternative Process Y

The method of Alternative Process X, wherein the act of determining whether a test sensor is positioned in the at least one opening includes the detector detecting that the test sensor is positioned in the at least one opening.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention claimed is:

1. A method of using a device configured to determine an analyte concentration of a fluid sample using a test sensor, the method comprising the acts of:
providing a device comprising a display, at least one user-interface mechanism, a device link configured to connect the device to a second device, a body portion including at least one opening formed therein, and a memory configured to store data;
connecting the device to the second device using the device link;
interacting with the at least one user-interface mechanism, the at least one user-interface mechanism being configured to assist in displaying the data on the display;
determining whether a test sensor is positioned in the at least one opening; and
if a test sensor is positioned in the at least one opening, inhibiting the data from being displayed on the display.

2. The method of claim 1, wherein the data includes a plurality of stored analyte concentrations.

3. The method of claim 1, wherein the device is connected to the second device using a cable.

4. The method of claim 1, further comprising transmitting, using the device link, the data to the second device.

5. The method of claim 4, wherein the device link is a wireless link.

6. The method of claim 1, further comprising the act of, if a test sensor is not positioned in the at least one opening, displaying the data on the display.

7. The method of claim 1, further comprising the act of, upon removal of the test sensor, allowing the data to be displayed on the display.

8. The method of claim 1, wherein the device further includes a software component configured to inhibit the data from being displayed on the display.

9. A method of using a device configured to determine an analyte concentration of a fluid sample using a test sensor, the method comprising the acts of:
providing a device comprising a display, at least one user-interface mechanism, a device link configured to connect the device to a second device, a body portion including at least one opening formed therein, and a memory configured to store data;
interacting with the at least one user-interface mechanism, the at least one user-interface mechanism being configured to assist in displaying at least a portion of the data on the display;
determining whether a test sensor is positioned in the at least one opening; and
if a test sensor is positioned in the at least one opening, inhibiting the data from being displayed on the display.

10. The method of claim 9, wherein the data is configured to be transferred to the second device using the device link.

* * * * *